(12) United States Patent
Carroll et al.

(10) Patent No.: US 7,955,298 B2
(45) Date of Patent: Jun. 7, 2011

(54) DEFINED DEFLECTION STRUCTURE

(75) Inventors: Sean Carroll, Beaconsfield (CA);
Domenic Santoianni, Kirkland (CA);
Benoit Thibault, St-Zotique (CA); Dan Wittenberger, Pierrefonds (CA);
Mathieu-Philippe Aubert,
Saint-Laurent (CA); Marc-André Marcotte, Outremont (CA)

(73) Assignee: Medtronic Cryocath LP, Toronto, Ontario (CA)

( * ) Notice: Subject to any disclaimer, the term of this patent is extended or adjusted under 35 U.S.C. 154(b) by 1544 days.

(21) Appl. No.: 11/112,100

(22) Filed: May 9, 2005

(65) Prior Publication Data

US 2005/0209557 A1 Sep. 22, 2005

Related U.S. Application Data

(60) Division of application No. 10/002,957, filed on Nov. 1, 2001, now Pat. No. 6,890,329, which is a continuation-in-part of application No. 09/596,227, filed on Jun. 15, 2000, now Pat. No. 6,585,717.

(60) Provisional application No. 60/139,193, filed on Jun. 13, 1999.

(51) Int. Cl.
*A61M 31/00* (2006.01)
(52) U.S. Cl. .................................... 604/95.04
(58) Field of Classification Search ............... 604/95.01, 604/523–528, 164, 95.02, 95.03, 95.04, 95.05
See application file for complete search history.

(56) References Cited

U.S. PATENT DOCUMENTS

| | | | | |
|---|---|---|---|---|
| 2,472,485 A | * | 6/1949 | Krippendorf | 138/118 |
| 3,416,531 A | * | 12/1968 | Lowell | 604/95.04 |
| 4,686,963 A | * | 8/1987 | Cohen et al. | 600/141 |
| 5,199,950 A | | 4/1993 | Schmitt et al. | |
| 5,273,535 A | * | 12/1993 | Edwards et al. | 604/95.01 |
| 5,275,152 A | * | 1/1994 | Krauter et al. | 600/129 |
| 5,329,923 A | | 7/1994 | Lundquist | |
| 5,571,085 A | | 11/1996 | Accisano | |
| 5,656,029 A | | 8/1997 | Imran et al. | |
| 5,782,828 A | * | 7/1998 | Chen et al. | 606/42 |
| 5,820,591 A | * | 10/1998 | Thompson et al. | 604/95.01 |
| 6,198,974 B1 | | 3/2001 | Webster, Jr. | |
| 6,450,948 B1 | | 9/2002 | Matsuura et al. | |

FOREIGN PATENT DOCUMENTS

| | | |
|---|---|---|
| DE | 4222271 A1 | 7/1992 |
| DE | 4222271 A1 | 1/1994 |
| EP | 0489937 A1 | 6/1992 |
| EP | 0898940 A1 | 3/1999 |
| EP | 0904797 A2 | 3/1999 |
| WO | WO9215356 | 9/1992 |
| WO | WO0076570 A2 | 12/2000 |

* cited by examiner

*Primary Examiner* — Manuel A Mendez
(74) *Attorney, Agent, or Firm* — Christopher & Weisberg, P.A.

(57) ABSTRACT

Deflection mechanisms are disclosed that are positionable to deflecting portions of a flexible body, such as a catheter, in more than one direction in a single plane, as well as in more than one plane. The invention allows a distal portion of a catheter to be deflected more than 360 degrees to provide a loop.

17 Claims, 11 Drawing Sheets

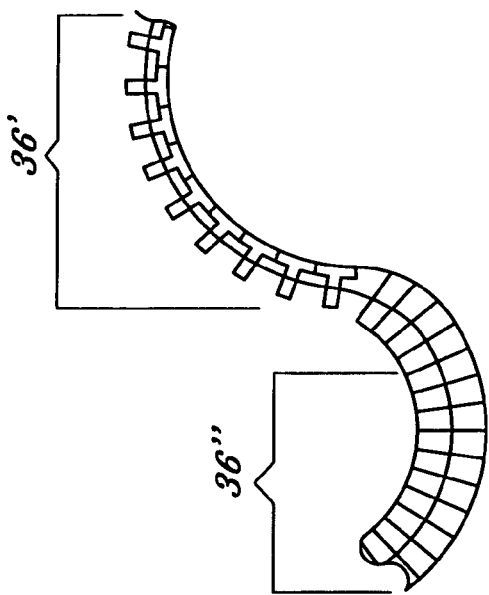
FIG. 3B
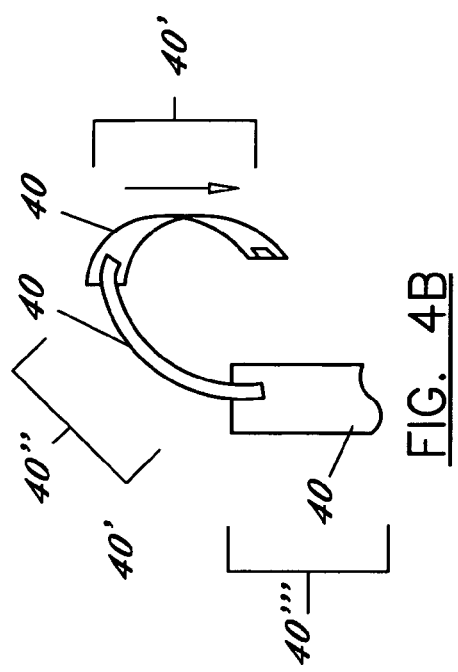
FIG. 3C
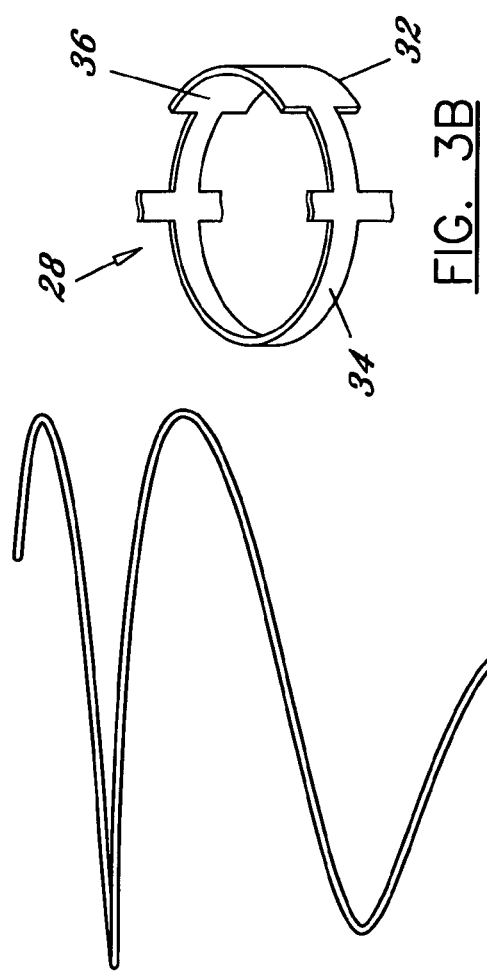
FIG. 3D
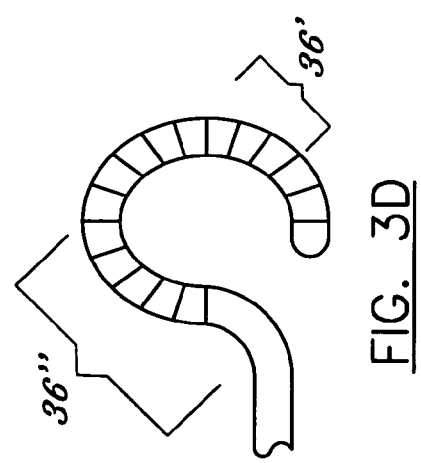
FIG. 4B
FIG. 1A

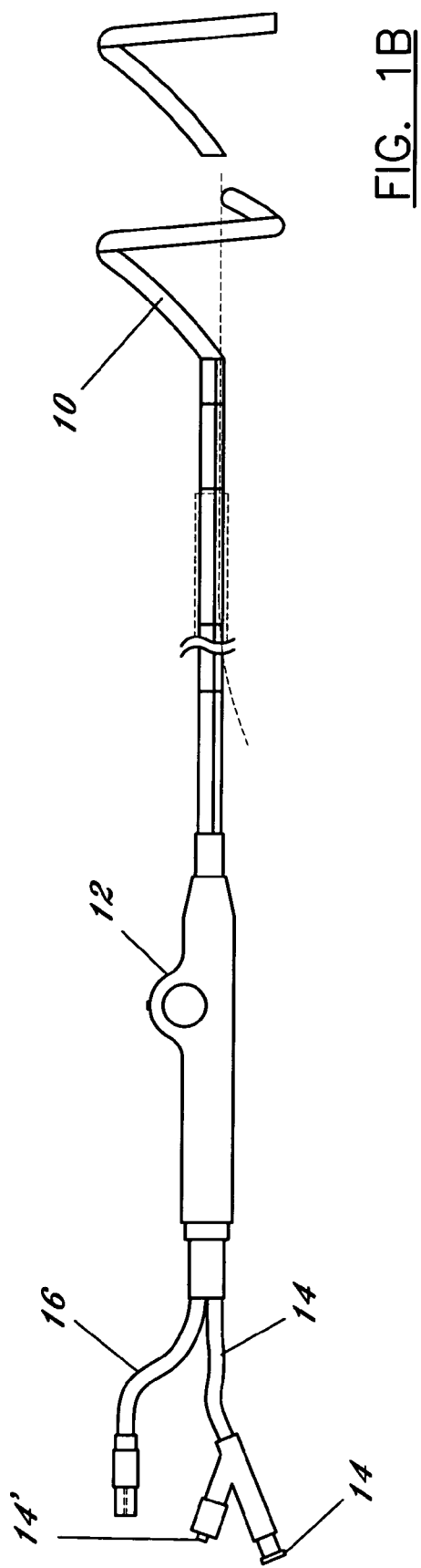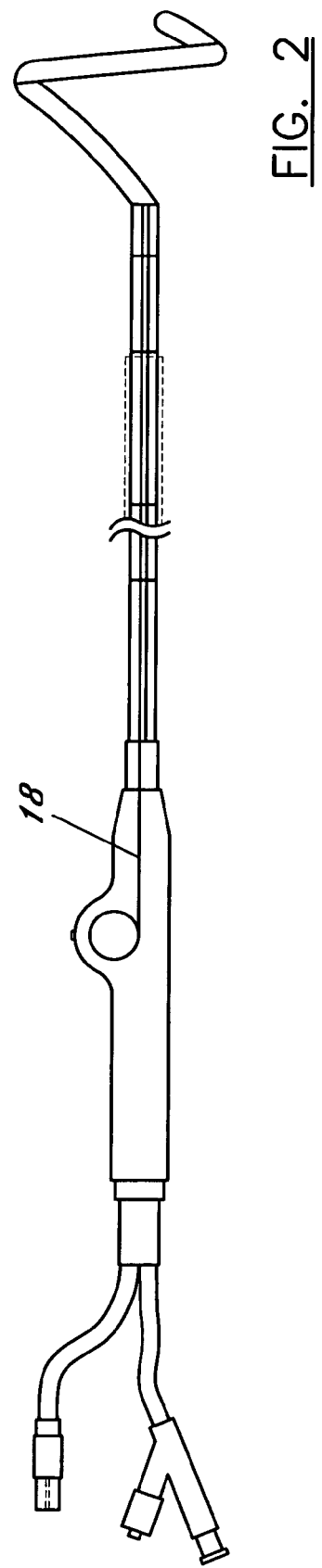

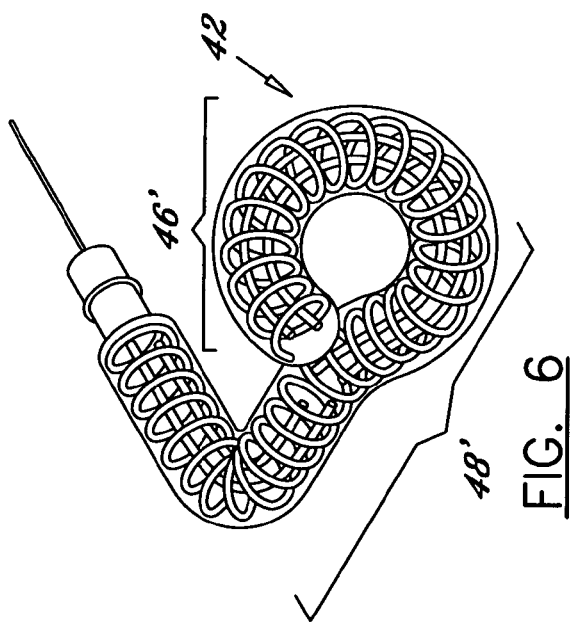
FIG. 6
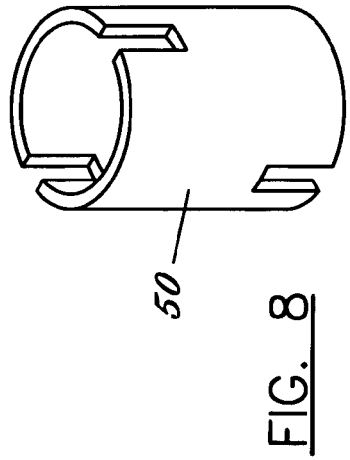
FIG. 8
FIG. 5
FIG. 7
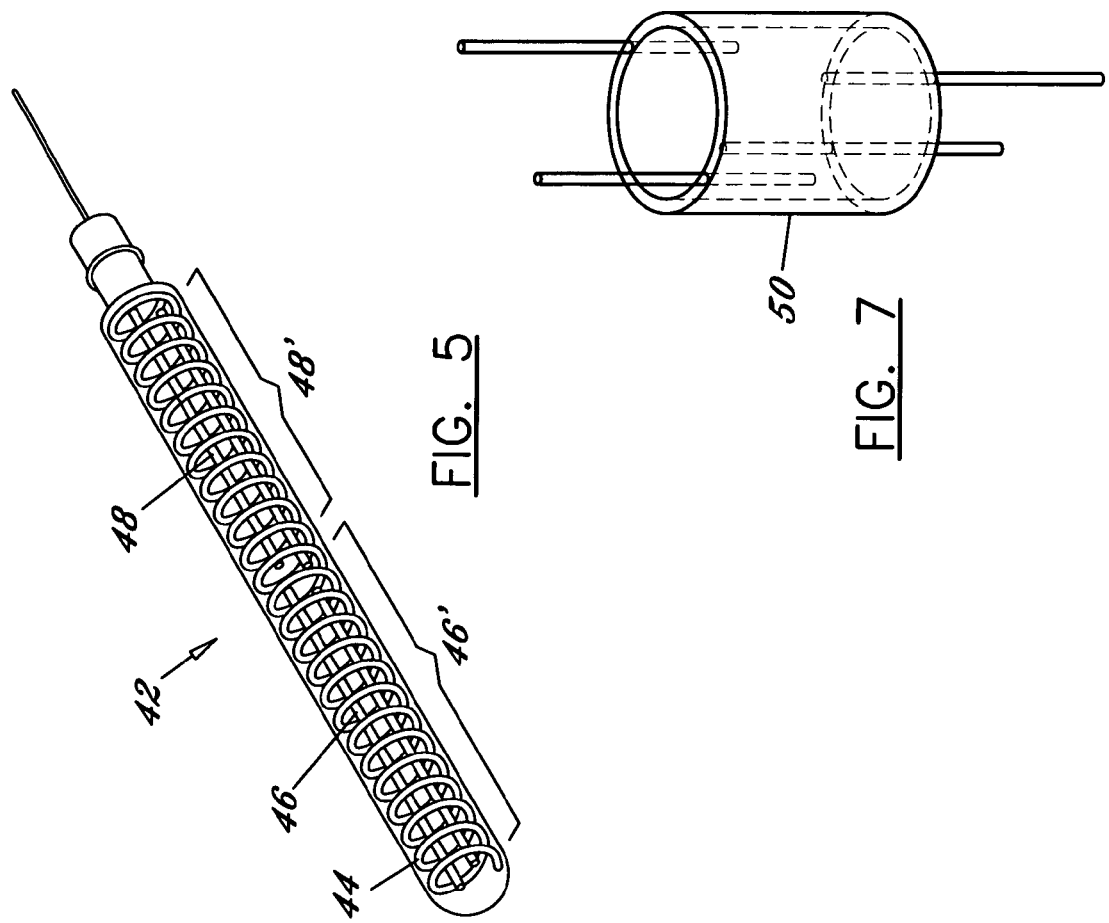

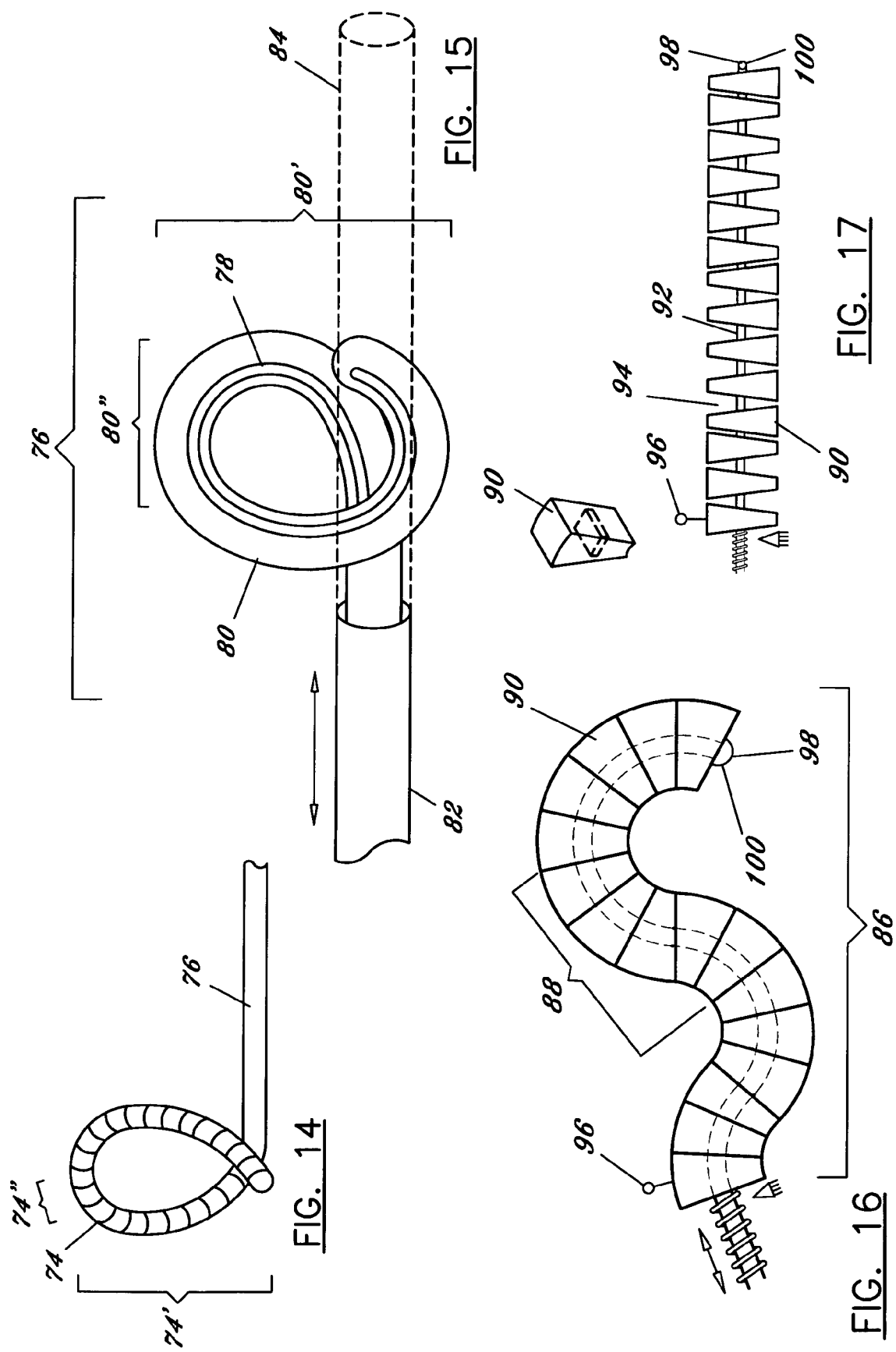

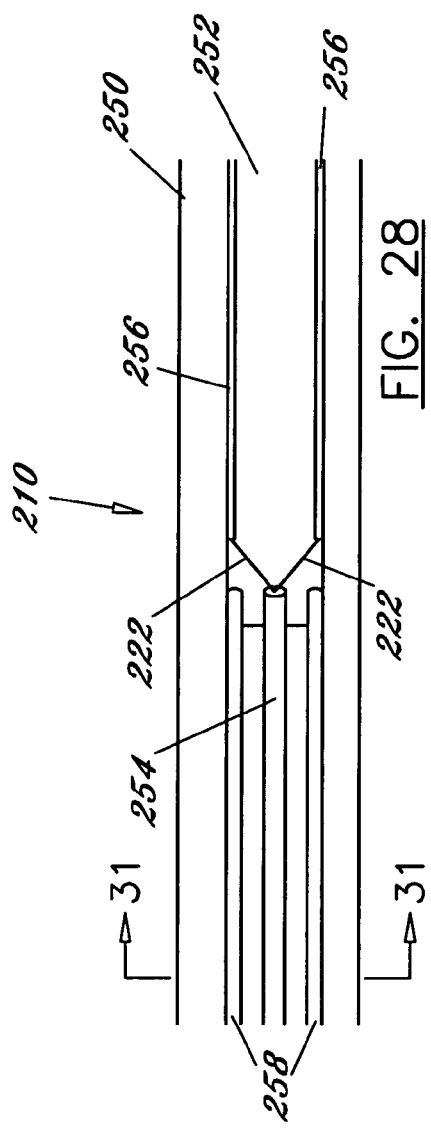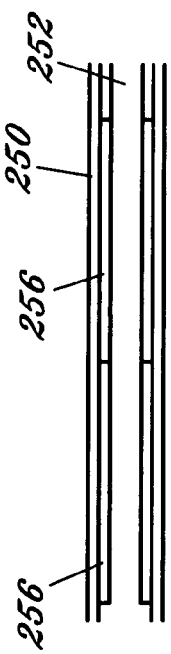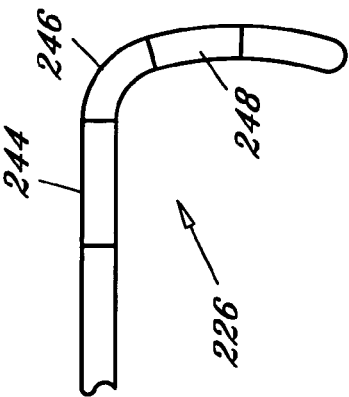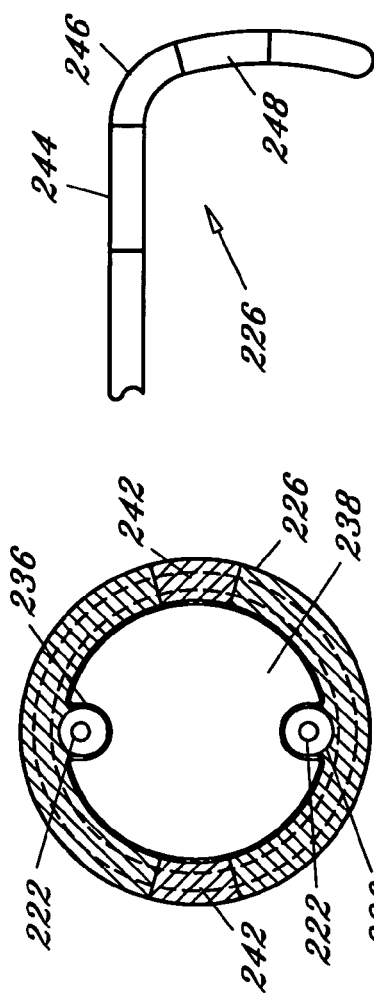

DEFINED DEFLECTION STRUCTURE

CROSS-REFERENCE TO RELATED APPLICATIONS

This application is a divisional application of application Ser. No. 10/002,957, filed Nov. 1, 2001 now U.S. Pat. No. 6,890,329, entitled APPARATUS AND METHOD FOR FORMING A CURVILINEAR LESION, which application is a continuation-in-part of and claims priority from U.S. Utility patent application Ser. No. 09/596,227, filed Jun. 15, 2000, entitled DEFLECTION STRUCTURE, now issued U.S. Pat. No. 6,585,717, which application is related to and claims priority from U.S. Provisional Patent Application Ser. No. 60/139,193, filed Jun. 15, 1999, entitled ANNULAR LESION CRYOCATHETER, now expired, the entirety of all of which are incorporated herein by reference.

STATEMENT REGARDING FEDERALLY SPONSORED RESEARCH

Not applicable.

FIELD OF THE INVENTION

The present invention relates to medical devices, and more particularly to steerable catheters.

BACKGROUND OF THE INVENTION

Minimally invasive surgery is commonly performed by inserting relatively small instruments into the body, as well as organs within the body, through one or more very small incisions. Many instruments are rigid and are directed to a site of interest by angling the instrument through the incision and inserting the device to a selected depth within the body. However, rigid instruments are unacceptable for many procedures, and even less invasive procedures have been developed that employ flexible catheter-based instruments. Although early catheter devices simply followed the contours of a body passage, such as a blood vessel to a selected treatment site, catheters with movable tip portions were developed to provide simple catheter steering.

The present steerable catheters most commonly include one or more wires that are anchored at a first point near the distal tip of the catheter and at a second point at the proximal end of the catheter or in a handle unit. A lever or knob is actuated to apply or reduce tension on the one or more wires causing the distal tip of the catheter to be pulled in the direction of the tension. Although steering mechanisms such as these have provided excellent results, it is believed that even greater steering or deflection control would further increase the possibilities for new surgical procedures. It would be especially desirable if existing and well developed pull-wire technology could be employed with new structures to provide such enhanced capability.

SUMMARY OF THE INVENTION

The present invention overcomes the limitations of known pull-wire steering mechanism to provide a deflection mechanism capable of deflecting portions of a flexible body, such as a catheter, in more than one direction in a single plane, as well as in more than one plane. The invention allows a distal portion of a catheter to be deflected more than 360 degrees to provide a loop.

In an exemplary embodiment, a deflection mechanism for a medical device includes rings and a connecting structure connecting the rings. The connecting structure can include a unitary structure or rod segments that connect adjacent rings. A second connecting structure can be provided that is radially spaced apart from the first connecting structure. A second group of rings, joined by another connecting mechanism can be provided so that the first rings deflect in a first plane and the second rings deflect in a second plane.

In another embodiment, a deflection mechanism for a medical device includes three planar shims defining three planes. Adjacent planar shims are joined so that the planes defined by each respective shim are different.

Yet another embodiment of a deflection mechanism for a medical device includes a deflection body having a longitudinal axis and two sets of longitudinal elements secured to the deflection body at different locations.

Still another embodiment of the invention includes a catheter having a distal end and a set of helically twisted elements extending longitudinally through the catheter proximate the distal end.

Another embodiment of the invention includes a catheter, a shape biased member disposed within the catheter, and a sheath slidably disposed over the catheter.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIG. 1A is a side view of a deflected catheter body in accordance with the invention;

FIG. 1B is a side view of a catheter system in accordance with the invention;

FIG. 2 is a side view of another catheter system in accordance with the invention;

FIG. 3B is a perspective view of an aspect of the embodiment of FIG. 3A in accordance with the invention;

FIG. 3C is a perspective view of an aspect of the embodiment of a deflection structure shown in FIG. 3A of a catheter in accordance with the invention shown in an actuated multi-plane state;

FIG. 3D is a perspective view of an embodiment of a deflection structure in an actuated multi-plane state in accordance with the invention;

FIG. 4B is a deconstructed perspective view of the embodiment of FIG. 4A in an actuated multi-plane state in accordance with the invention;

FIG. 5 is a perspective view of another embodiment of a deflection structure of a catheter in accordance with the invention shown in a non-actuated state;

FIG. 6 is a perspective view of an embodiment of a deflection structure of a catheter in accordance with the invention shown in an activated state;

FIG. 7 is a view of a coupling in accordance with the invention;

FIG. 8 is an exploded view of another coupling in accordance with the invention;

FIG. 14 is a perspective view of another embodiment of a deflection structure of a catheter in accordance with the invention shown in an actuated multi-plane state;

FIG. 15 is a partial cross-sectional view of another embodiment of a catheter in an actuated multi-plane state in accordance with the invention;

FIG. 16 is a side view of another embodiment of a deflection structure of a catheter in accordance with the invention in an actuated multi-plane state;

FIG. 17 is a side view of the embodiment of FIG. 16 shown in a non-actuated state;

FIG. 26 is a sectional view of the deflection structure of FIG. 21 taken along line 24-24;

FIG. 27 is a side view of an alternate deflection structure in accordance with the present invention;

FIG. 28 is a sectional view of a body of the catheter in accordance with the present invention taken along line 28-28 of FIG. 21;

FIG. 29 is an alternate sectional view of a body of the catheter in accordance with the present invention taken along line 28-28 of FIG. 21;

DETAILED DESCRIPTION OF THE INVENTION

Figure 3A:
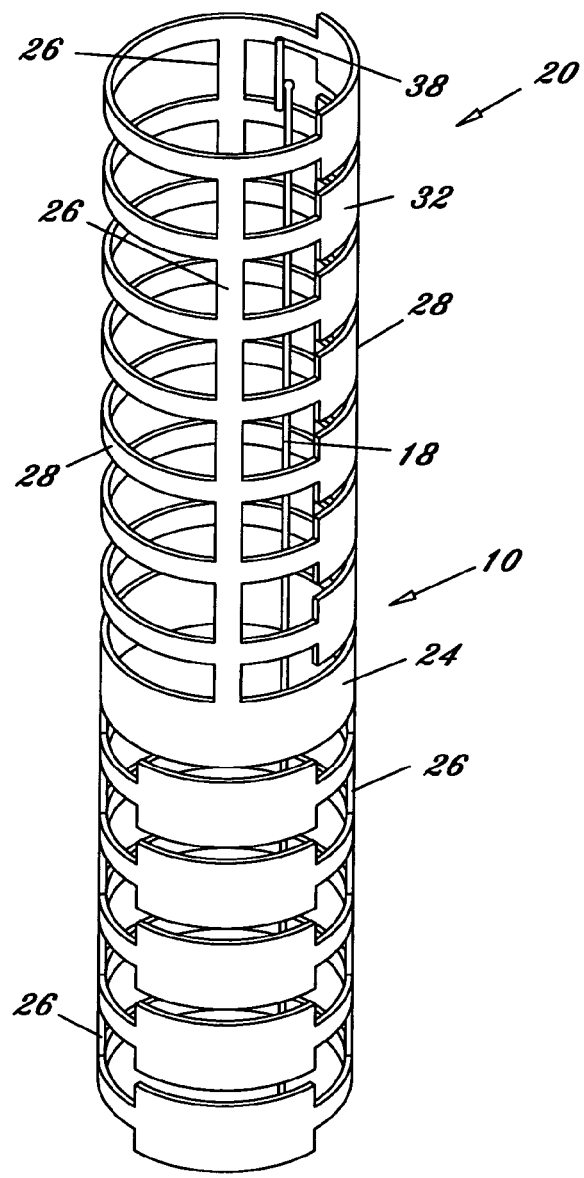
FIG. 3A is a perspective view of an embodiment of a deflection structure of a catheter in accordance with the invention.

The inventive deflection features disclosed herein have applicability to any flexible body, such as a catheter-based surgical device and references to specific systems or procedures are merely exemplary.

FIG. 1B shows a catheter system in accordance with the invention. The system includes a catheter body 10 that is shown in an actuated or deflected state or condition. In this illustration, the catheter is configured so that the distal region of the catheter body 10 deflects in more than one plane to provide a "cork-screw" or helical tip region. Although a screw shape is shown, the catheter can be configured to provide other complex configurations. It should also be understood that the catheter can be actuated and used though a range of deflections at points other than a maximally deflected configuration. In other words, the system is not simply a two-state system (no deflection/full deflection).

FIG. 1A illustrates a catheter body 10 having multiple loops, wherein the distal end of the catheter is deflected well in excess of 360 degrees.

Deflection structures or mechanisms for the present catheter system are described in greater detail below, and are compatible for use with catheters such as those disclosed in U.S. Pat. Nos. 5,899,898 and 5,899,899 to Arless et al., which are incorporated herein by reference.

Continuing to refer to FIG. 1B, the system also includes a handle 12. First and second umbilicals 14 and 16, respectively, can be provided to connect the handle 12 to a console (not shown) that supports the surgical function of the selected device. For example, the first umbilical 14 can provide a path for a liquid or gas refrigerant to be transferred between the console and the handle 12; and the second umbilical 16 can provide a signal path, such as for electrical signals, between the console and the handle. Additional umbilicals can be provided as required, and the functions of more than one umbilical can be provided in a single, multifunction umbilical. Also, one or more of the umbilicals can be divisible into two or more portions as shown in FIG. 1B, wherein the first umbilical includes portion 14 and 14'.

FIG. 2 depicts an exemplary embodiment as shown in FIG. 1B which further includes a pull-wire 18. Although the present invention can use pull-wires to cause deflection, as discussed below, additional structures are provided that cause the deflection to produce a shape other than a simple, single plane bend. Further, although a pull-wire(s) can be used to cause deflection, the disclosed structures can be associated with other movement mechanisms to provide the inventive configurations.

Referring now to FIG. 3A, additional details of an exemplary deflection structure or mechanism are discussed in greater detail. A catheter body 10 is shown in a de-constructed view so that a deflection structure 20 can be more easily understood. The deflection structure 20 comprises a tip 22 connected to an intermediate point 24 by a connecting structure, which forms a distal deflection group. In this embodiment the connecting structure includes first and second flexible connecting rods 26. Disposed along connecting rods 26 are multiple rings 28, each defining a plane. Each ring 28 is aligned with a plane that is substantially perpendicular to a longitudinal axis of the connecting rods 26 when in a non-actuated state as shown in FIG. 3A. Connecting rods 26 can also be represented by a plurality of rod segments that connect rings 28. Additionally, a pull-wire 18 is disposed within the deflection structure 20. Referring now to an enlarged view in FIG. 3B, the asymmetrical rings 28 have a first half 32 and a second half 34. The first half 32 includes a flattened, curved portion or shaped spine section 36.

Referring again to FIG. 3A, operation of the device is now discussed. Tension is applied to the pull-wire 18, which is attached at a point 38 in the tip 22, thereby causing the deflection structure 20 to bend toward the first half 32 of the rings 28. The tension can be applied until a full actuation state occurs and the individual spine sections 36 contact one another as shown in FIG. 3C. In the full actuation state the deflection structure 20 takes a pre-determined shape that is defined by the specific physical construction of the individually shaped spine sections 36 to define a first deflection plane. Additionally, more shaped spine sections 36 may be located proximal to the intermediate point 24 with a similar arrangement as described above, further defining a second deflection plane, which is different than the first deflection plane. The first and second deflection planes are aligned radially different from one another. FIG. 3C shows the first deflection plane 36' and the second deflection plane 36".

Additional discrete deflection structure sections can be added to the catheter tip to form other desired deflection shapes. An exemplary resultant shape of the catheter body in a full actuation state is shown in FIG. 3D. Shown are the first deflection plane 36' and the second deflection plane 36".

The above described structure may be formed from one piece of material or from multiple pieces and then secured together by methods known in the art. For example, a one piece assembly can be manufactured using a laser machining The material can be a super-elastic spring steel, a polymer or any other suitable material.

Figure 4A:
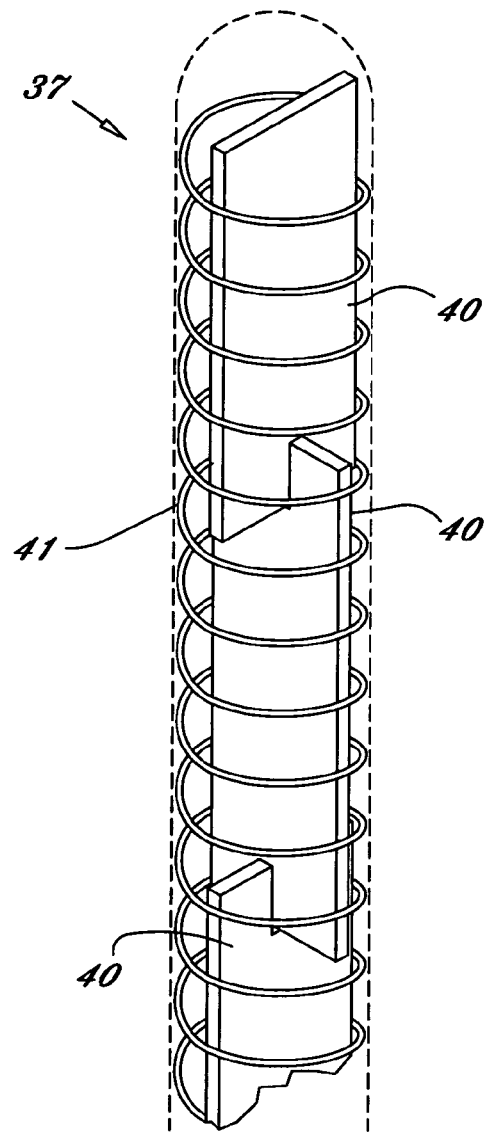
FIG. 4A is a perspective view of another embodiment of a deflection structure of a catheter in accordance with the invention.

Turning now to FIG. 4A, another exemplary embodiment of a deflection structure for a catheter is shown and discussed in greater detail. Shown is a deflection structure 37 having first, second and third planar shims 40. Each planar shim 40 is a flat elongate piece of material with ends, and that define discrete planes. Each of the planar shims 40 are joined to one another at their ends and are aligned in a different plane relative to each other. When actuated, each of the deflection shims will bend in a deflection plane that is substantially perpendicular to the shim's plane and will form a pre-determined actuation shape. Further, a coil 41 can be disposed around at least a portion of the joined planar shims 40.

For example, FIG. 4B shows a deconstructed view of the deflection structure of FIG. 4A in an actuated state, planar shims 40 are each actuated in a separate plane. Shown is a first deflection plane 40', a second deflection plane 40" and a third deflection plane 40'". The actuation of the deflection shims 40 can be accomplished by one or more pull-wires disposed within the deflection mechanism and attached at various locations to effect different final and intermediate configurations. The planar shims 40 can be joined in many different ways, for example, they may be slotted and fitted together or they may be welded together. The planar shims can be constructed from a spring material and actuation may be accomplished by applying tension supplied by one or more pull-wires, or by constructing the planar shims from a shape-memory material and applying that materials' required means, as is known in the shape-memory art. For example, inducing a temperature change in the material can cause it to assume a preset shape.

Turning now to FIG. 5, another exemplary embodiment of a deflection structure for a catheter is shown and discussed in greater detail. Shown is a deflection body 42. Disposed within an optional helical coil 44 are a first set 46 and second set 48 of longitudinal elements arranged substantially parallel to a longitudinal axis of deflection body 42. The helical coil 44 helps to maintain a relatively straight configuration of the deflection structure when in a non-actuated state. The first set 46 and second set 48 of longitudinal elements each define an independent plane of deflection, a first deflection plane 46' and a second deflection plane 48' respectively, when actuated. A junction 50 defines the relative radial angle of alignment of the sets of longitudinal elements.

FIG. 7 and FIG. 8 show detailed views of a junction 50 that can be used to join the first and second sets of longitudinal elements at different radial angles relative to one another. The longitudinal elements can be manufactured from a spring material and actuation can be accomplished by applying tension with one or more pull-wires, or by constructing the longitudinal elements from a shape-memory material and applying that materials' required means, such as temperature.

FIG. 5 shows the deflection structure 42 in a non-actuated state. When the deflection structure is actuated it assumes a pre-determined shape, for example, as shown in FIG. 6.

Figure 9:
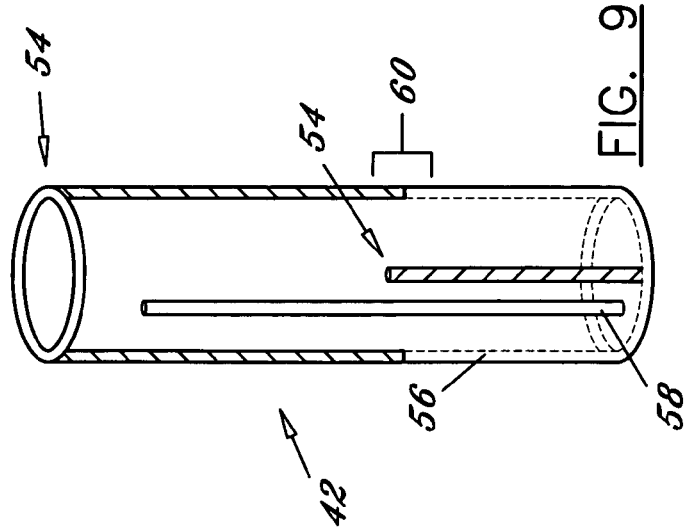
FIG. 9 is a partial cross-sectional view of another embodiment of a deflection structure of a catheter in accordance with the invention.

Turning now to FIG. 9, another exemplary embodiment of a deflection structure for a catheter is shown and discussed in greater detail. This embodiment comprises a series of longitudinal elements 54 embedded or attached to a flexible tube 56. The longitudinal elements 54 are constructed of a spring material or a shape-memory material. When tension is applied to a pull-wire 58 or alternatively when the actuating mechanism of the shape memory material is applied, the longitudinal elements 54 deflect in different planes to assume an actuation state as shown in FIG. 14. The relative radial angle of multiple sets of longitudinal elements 54 can be controlled to specifically define final or intermediate actuation state shapes according to application demands.

Figure 11:
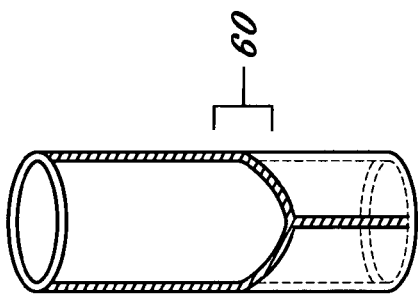
FIG. 11 is a partial cross-sectional view of another embodiment of a deflection structure of a catheter in accordance with the invention.
Figure 10:
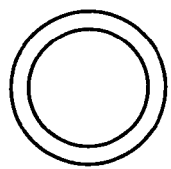
FIG. 10 is a sectional end view of an embodiment of a deflection structure of a catheter in accordance with the invention.

Different embodiments of a transition zone 60 can be seen in FIGS. 9, 10 and 11. Transition from one plane to another can be immediate or gradual. Further, a junction 50 as seen in FIGS. 7 and 8 can be used.

Figure 12:
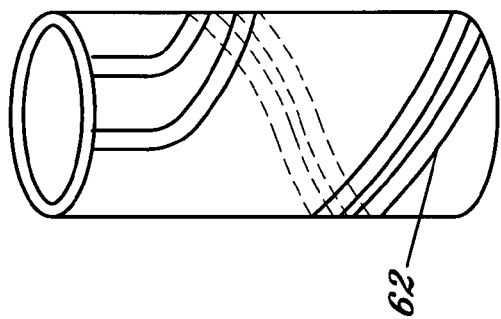
FIG. 12 is a partial cross-sectional view of another embodiment of a deflection structure of a catheter in accordance with the invention.

Additionally, as seen in FIG. 12, a coiled element set 62 can be used to create an uncoiling action upon actuation resulting in an actuation state as seen in FIG. 14. Again, the final actuation state can be predetermined to suit application demands by the manufacturer.

Figure 13:
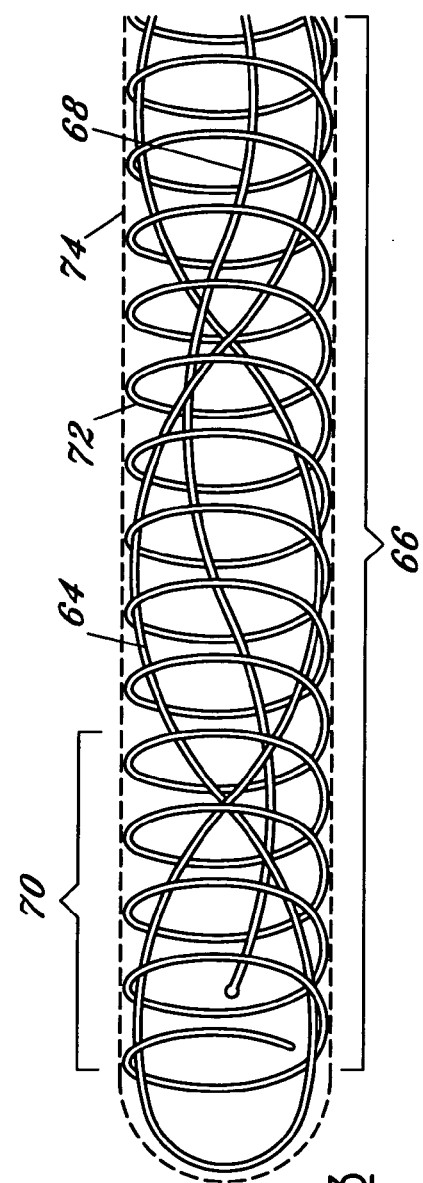
FIG. 13 is a partial cross-sectional view of another embodiment of a catheter in accordance with the invention.

Shown in FIG. 13, is a set helically twisted elements 64 having a continuous helical-shaped twist contained inside a deflection body 66. A pull-wire 68 is attached to a distal end 70 of the deflection body 66. A wire coil 72 encloses the assembly and supports a membrane 74. The coil 72 prevents the pull-wire 68 from "straightening" when in a non-actuated state. When a pull tension is applied to the pull-wire 68, the struts 64 are deflected in a plane perpendicular to the struts, in a continuously rotating direction. The final shape of the distal end 70 is a ring 74 configured perpendicular to the catheter shaft 76, as seen in FIG. 14. The plane in which the distal end 70 moves to the ring 74 can be made to be in a plane perpendicular to the shaft, depending on the pitch and number of twists. FIG. 14 shows a first deflection plane 74' and a second deflection plane 74".

Turning now to FIG. 15, another exemplary embodiment of a deflection structure for a catheter is shown and discussed in greater detail. The deflection structure 76 comprises a shape biased member 78 included in a distal section of a catheter tip 80, and a sheath 82 that houses the catheter tip 80 until the place and time of actuation. The shape biased member 78 has a pre-determined shape and can be reversibly conformed to a non-actuated state 84 by sliding the sheath 82 over it. When the sheath 82 is partially withdrawn from the catheter tip 80 or the catheter tip 80 is advanced relative to the sheath 82, the shape biased member 78 assumes its pre-determined shape and is thus actuated. The shape biased member 78 may be made of polymer, a spring-tempered stainless or super-elastic alloy that when released from the sheath 82 will force the catheter tip 80 to take the shape desired. FIG. 15 shows a first deflection plane 80' and a second deflection plane 80".

Another embodiment as disclosed in FIG. 16 shows a deflection structure 86 which comprises a plurality of curves 88 with a pre-established deflection shape. Turning to FIG. 17, a series of beveled-faced elements 90 are placed over one or more wires 92 (either rectangular section wire or a set of round wires). Initially the beveled-faced elements 90 are free-floating on the wires 92, with small intervals 94 in between each element 90. When a pull tension is applied to the wires 92, a first element 96 will be pressed against a fixed point 98 at the deflection structure tip 100, and subsequently each of the remaining elements 90 will be pulled close together until all the beveled facets are in contact with one another, thereby imparting a specific angular abutment to the catheter tip in a pre-established shape. The pre-established shape depends on the sequence of angles on the faces of the elements and their predetermined configuration. FIG. 16 shows an exemplary actuation shape.

Figure 18:
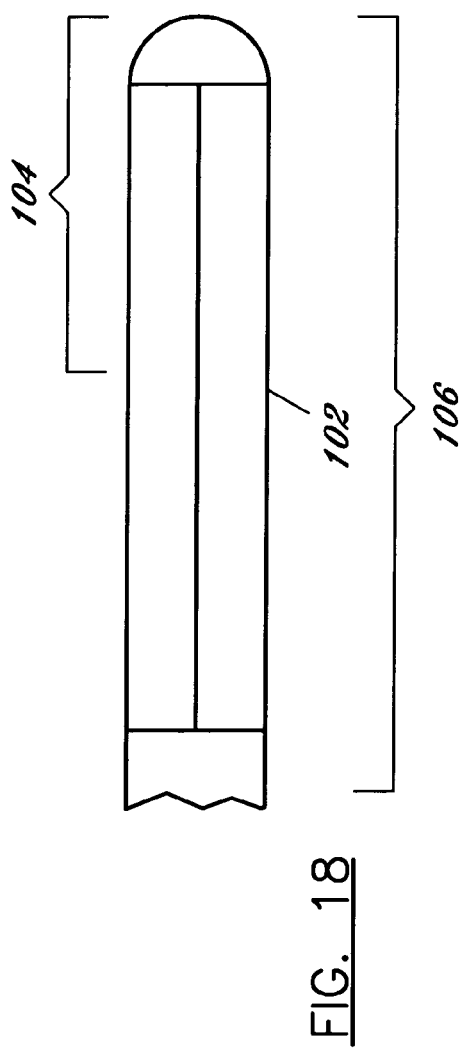
FIG. 18 is a side view of another embodiment of a deflection structure of a catheter in accordance with the invention, shown in a non-actuated state.
Figure 20:
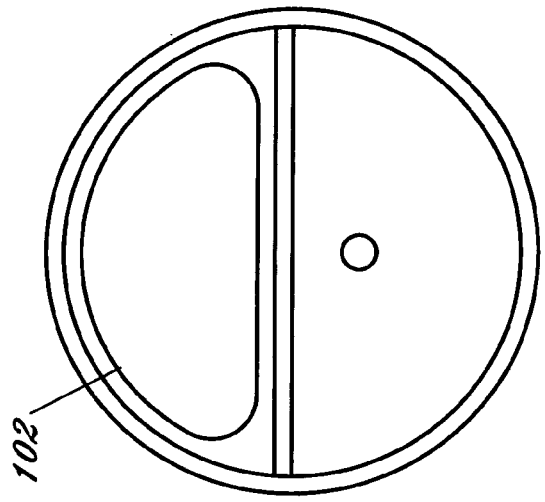
FIG. 20 is an end cross-sectional view of the embodiment shown in FIGS. 18 and 19.
Figure 19:
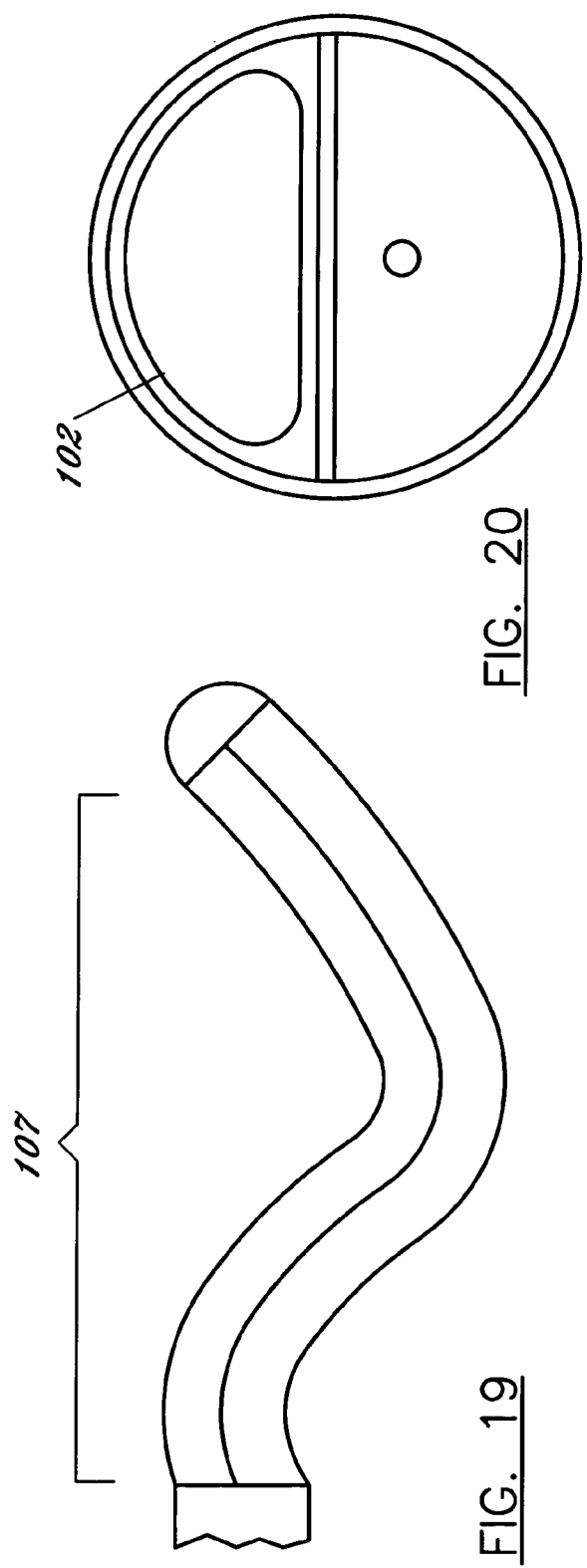
FIG. 19 is a side view of the embodiment shown in FIG. 18, shown in an actuated multi-plane state.

Another exemplary embodiment as shown in FIG. 18 comprises a preformed balloon insert 102 placed in a distal segment 104 of a catheter tip 106 which upon inflation conforms the catheter tip to a predetermined profile 107 as seen in FIG. 19. Additionally, the preformed balloon insert 102 acts as an insulation material. The preformed balloon insert 102 is constructed from a non-compliant balloon that is preformed by blow-molding and/or thermally setting or by other suitable means to a defined shape. The preformed balloon insert 102 is housed in a distal end of a catheter 10 as seen in FIG. 1. After being placed close to the target tissue, the preformed balloon insert 102 is inflated with a non-compressible, biocompatible liquid through an inflation lumen (not shown). The preformed balloon insert 102 will force the catheter tip 104 to take its shape. The preformed balloon insert 102 has a triple role, shaping the tip, increasing rigidity, and shielding the catheter's dorsal side from unwanted heat.

Figure 21:
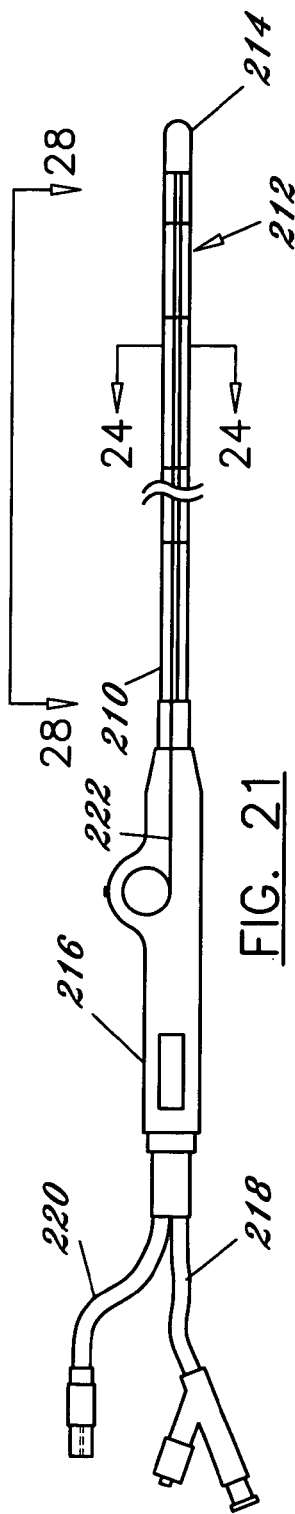
FIG. 21 is a side view of a catheter system including a deflection structure in accordance with the invention shown in a non-actuated state.

Now referring to FIG. 21 an alternate exemplary embodiment of a catheter system as described in FIGS. 5 and 6 above is discussed in more detail. The system includes a catheter body 210, a deflection region 212 and a distal region 214, all having a longitudinal axis. The deflection region 212 is shown in a resting or non-deflected state or condition. The catheter can be configured to provide various pre-defined deflection shapes. Further, various distal region arrangements can be used in combination with the deflection region of the invention.

The system also includes a handle 216. First and second umbilicals 218 and 220, respectively, can be provided to connect the handle 216 to a console (not shown) that supports the surgical function of the selected device. For example, the first umbilical 218 provides a path for a liquid or gas refrigerant to be transferred between the console and the handle and the second umbilical 220 provides a signal path, such as for electrical signals, between the console and the handle. Additional umbilicals can be provided as required, and the functions of more than one umbilical can be provided in a single, multifunction umbilical. Also, one or more of the umbilicals can be divisible into two or more portions as shown in FIG. 21, wherein the first umbilical includes two portions of umbilical 218 such as for fluid infusion into the catheter and a vacuum for the excavation of the fluid. Further, one or more actuator members 222 can be disposed within the catheter body 210. For example, a pull wire, a tape or any other suitable structure for applying a force.

Figure 22:
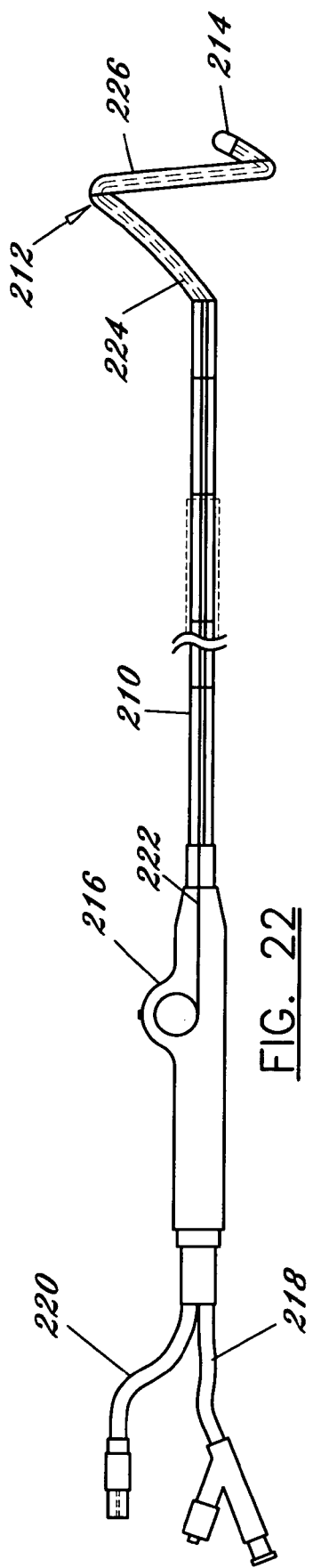
FIG. 22 is a side view of the catheter system of FIG. 21 shown in an actuated state.

Turning now to FIG. 22, the catheter system of FIG. 21 is shown in an actuated state. The catheter system takes the actuated state when a force is applied via the actuator member 222. The plane of deflection and shape of the actuated state is dictated by the physical construction of the catheter system. More specifically, the plane of deflection and shape is dictated by the flexibility and density of the deflection region 212 and the presence and physical attributes of one or more longitudinal elements 224 adjacent or within the deflection region 212 (shown in phantom). The deflection region 212 is defined by a deflection wall 226 which is manufactured from a formable resilient material having a specific density and flexibility rating. The longitudinal elements 224, which are provided within or on the deflection wall 226, in combination with the actuator member 222 and the deflection wall 226 define the plane and shape of the deflection of the deflection region 212. In FIG. 22, two longitudinal elements 224 are shown in phantom, however, a lesser or greater number of elements can be provided. As will be more fully understood from the disclosure herein, the present invention provides a device that can dictate a predefined deflection plane and shape. In addition, the structure of the body 210 provides for torque transfer between the handle 216 and the deflection region 212 and thereby to the distal region 214.

Figure 23:
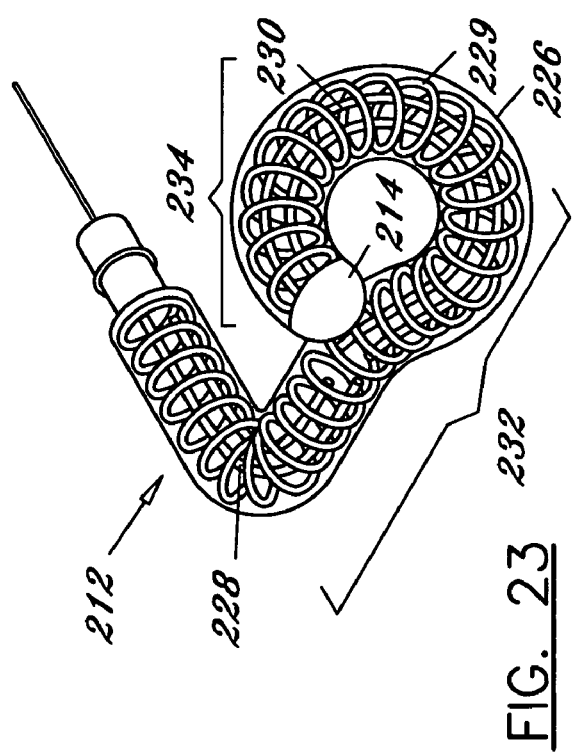
FIG. 23 is a perspective view of the deflection structure of FIG. 22.

Turning now to FIG. 23, an alternate exemplary embodiment of a deflection structure for a catheter is shown and discussed in greater detail. Shown is a deflection region 212 and distal region 214. Disposed within the deflection wall 226 are two sets of longitudinal elements 228 and 230 arranged substantially parallel to a longitudinal axis of deflection region 212. The first set 228 and second set 230 of longitudinal elements each define an independent plane of deflection, a first deflection plane 232 and a second deflection plane 234 respectively, when actuated. As shown in FIG. 23, the sets of longitudinal members can be radially aligned to define a specific defined deflection shape. It will be readily understood that more than or less than two sets of longitudinal elements can be employed to define the desired shape and that the sets can be radially aligned at any desired angle. The longitudinal elements 224 provide for a bias to the non-actuated state and partially define the plane of deflection. For example, if two longitudinal elements are radially aligned 180 degrees apart and an actuation force is applied, the structure will bend in a direction perpendicular to a combined longitudinal axis of the longitudinal elements. Further, the deflection plane and shape are defined by the relative rigidity or flexibility of the deflection wall 226. For example if a section of the wall is relatively rigid, the radius of bend at that section will be greater than that of a section having a less rigid composition. While multiple sets of longitudinal elements are shown in FIG. 23, for the purposes of explanation, one set of longitudinal members will be described hereafter. However, it is understood that any of the alternate exemplary embodiments discussed herein can employ one or more longitudinal elements. Also shown in FIG. 23 is an optional coil 229 which can be provided in any of the embodiments discussed herein. The coil 229 can extend the entire length of the catheter system or a some lesser portion thereof. The coil 229 provides for torsional transfer along the catheter system, resistance to compressional forces and can bias the system to a pre-determined shape. Further, it is contemplated that any set of radially aligned longitudinal elements 224 can be replaced by a flat planar shim having a length comparable to the longitudinal elements 224, whereby the edges of the shim provide similar functionality as the individual longitudinal elements 224.

Figure 24:
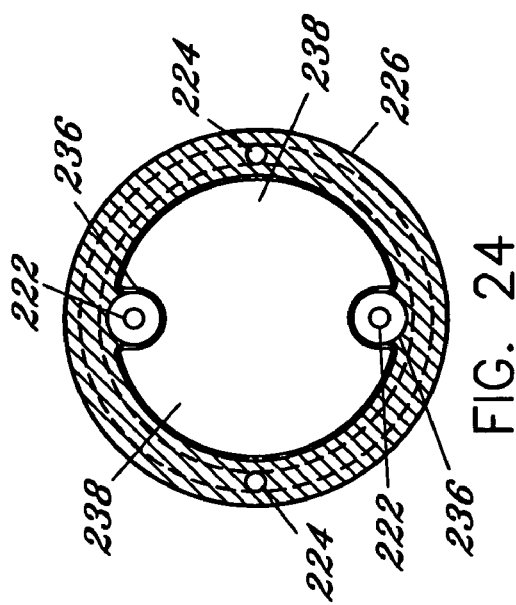
FIG. 24 is a sectional view of the deflection structure of FIG. 21 taken along line 24-24.

Turning now to FIG. 24, which is a sectional view taken along line 24-24 in FIG. 21, one embodiment of the deflection region is described in more detail. FIG. 24 shows longitudinal elements 224 positioned within deflection wall 226 and substantially aligned with the longitudinal axis of the deflection region 212. The longitudinal elements 224 have a fixed rigidity that is greater then the rigidity of the deflection wall 226. Located within a deflection conduit 236 are actuator members 222. FIG. 24 shows two longitudinal elements 224 aligned radially 180 degrees from one another on the deflection wall 226 and two deflection conduits 236 radially aligned 180 degrees from one another on the deflection wall 226. The longitudinal elements 224 can be embedded within the deflection wall 226 during formation of the deflection wall 226 or can be attached to a portion of the wall by commonly known adhesive methods or equivalent. Alternately, the longitudinal elements 224 can be affixed to an optional coil provided within the wall 226 or adjacent thereto. Likewise, the deflection conduits 236 can be embedded in the deflection wall 226 or be attached to the wall. It is contemplated that the radial alignment of the longitudinal elements can be from substantially 0 degrees to substantially 360 degrees depending on the desired deflection plane and shape. As such an alternate exemplary embodiment provides two longitudinal elements 224 positioned on the same "side" of the deflection wall 226 as one another, or less than 180 degrees from one another. This arrangement may be employed in any of the embodiments discussed herein. Further, one or more deflection conduits 236 and longitudinal elements 224 can be positioned in varying locations around deflection wall 226. As such, one or more longitudinal elements 224 are arranged to define a preferred deflection shape and/or plane. As discussed in more detail below, adjusting the rigidity of the deflection wall 226 affects a different radius of bend when a force is applied to the deflection region 212. It is contemplated that various materials may be used to construct the longitudinal elements 224. Several examples of suitable materials are NiTi, spring steel and carbon fiber. Also shown in FIG. 24 is a deflection lumen 238 which is defined by the deflection wall 226. The deflection lumen provides passage for both fluids and accessories between each end of the catheter system as is known in the art.

Figure 25:
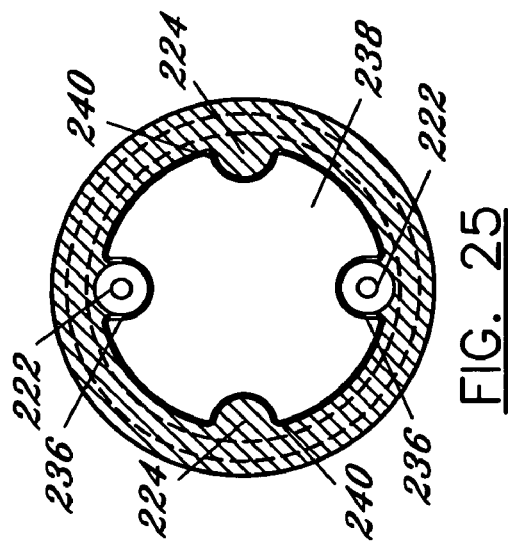
FIG. 25 is a sectional view of the deflection structure of FIG. 21 taken along line 24-24.

Turning now to FIG. 25, which is an alternate cross sectional view taken along line 24-24 in FIG. 21, another embodiment is discussed in more detail. In this embodiment a rib 240, having a length, is provided protruding into the deflection lumen 238 from the deflection wall 226 and extending either the length of the deflection region 212 or a lesser portion thereof. Further, longitudinal elements 224 are positioned within rib 240. Rib 240, is constructed from material that can have a varying rigidity along its length. By controlling the rigidity of the rib 240 during manufacturing, a preferred deflection shape can be defined by controlling bend radii along the length of the rib 240. By providing variable rigidity along the length of rib 240, variable resistance to a bending force is provided, thereby defining bend shape and plane of deflection. It will be readily understood that an area of the rib 240 with a greater rigidity will have a greater radius of bend compared to an area with a lesser rigidity which has a lesser radius of bend per unit force that is applied by the actuator member 222. As discussed above, one or more deflection conduits 236 and one or more longitudinal elements 224 can be provided at variable locations along the deflection wall 226. Thus, it has advantageously been found that deflection shape and deflection plane alignment can be defined by varying the rigidity of deflection wall 226 or rib 240 while maintaining a constant rigidity of the longitudinal elements 224.

Turning now to FIG. 26 which is another alternate cross sectional view taken along line 24-24 in FIG. 21, still another embodiment is discussed in more detail. In this embodiment wall section 242 is constructed to have a greater rigidity of structure when compared to the rigidity of deflection wall 226. Further, wall section 242 can either extend the length of the deflection region or a lesser portion thereof. This arrangement allows the wall section 242 to define a bend radii in a similar manner as the longitudinal element and deflection wall configuration provided above. Further, relative rigidity along the length of wall section 242 can be varied to specifically define a preferred deflection shape and/or deflection plane. For example, a deflection region where one section of the wall section 242 has a more rigid structure when compared to another section of the wall section 242 will defined a greater bend radius at the greater rigidity section than the lesser rigidity section, per unit force applied by the actuator member 222. Again, as discussed above, one or more deflection conduits 236 and one or more actuator members 224 can be provided along the deflection wall 226. The wall sections can be referred to as ribs and have various shapes as will be apparent from the disclosure of the present invention.

Turning now to FIG. 27, which shows an alternate embodiment discussed in more detail, where individual sections of the deflection wall 226 have different rigidity compared to other sections of the deflection wall 226. FIG. 27 shows a side view of a catheter system of the invention, in a preferred deflection state. First wall sub-section 244 has a different rigidity compared to second wall sub-section 246, and third wall sub-section 248 has a different rigidity compared to second wall sub-section 246. In this manner, many such sections may be arranged to provide areas with varying rigidity. It is contemplated that the boundary between different sections can be a smooth transition from one rigidity to another or in distinct transitions as shown here. In this embodiment, the longitudinal member has a constant rigidity along its length (not shown). As discussed above, by providing sections with different wall rigidity, the manufacturer can define the preferred deflection plane and shape. This manner of defining deflection plane and shape is easier to accomplish and less expensive than prior art methods. By controlling the density and/or rigidity of the wall section of the deflection region, the manufacturer controls the deflection parameters. It is also contemplated that the deflection wall 226 can have a constant rigidity to define a simple deflection pattern.

Figure 30:
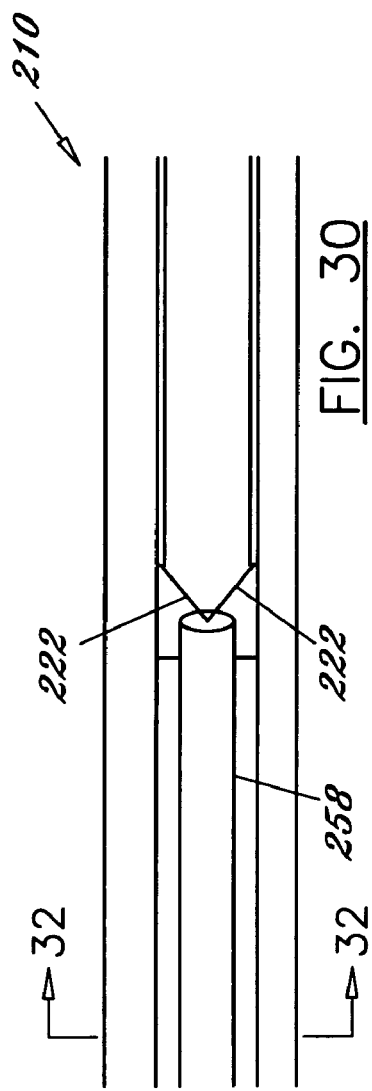
FIG. 30 is still another alternate sectional view of a body of the catheter in accordance with the present invention taken along line 28-28 of FIG. 21.

Turning now to FIG. 28, which is an alternate sectional view of an exemplary embodiment of the body 210 of the catheter taken along line 28-28 in FIG. 21. The body 210 has a wall 250 which defines a body lumen 252. The body lumen 252 is configured to pass fluids to and from each end of the catheter system. Further disposed within the body lumen 252 is a conduit 254. An actuator member 222 is disposed within the conduit 254 having a first end and a second end, wherein the first end is connected to an actuator within the handle and the second end is connected to an attachment point within the deflection region (not shown). The conduit 254 can either be provided in a central location as shown in FIG. 28 or along the wall 250 as shown in FIG. 29. The wall 250 further defines a hollow deflection conduit 256 which is configured to receive the actuator member 222. The deflection conduit 256 can alternatively run the entire longitudinal length of the wall 250 as shown in FIG. 29 or a portion thereof, as shown in FIG. 28. Alternatively, the deflection conduit 256 can be an integral formation of the wall 250, or can be a separate piece which is attached along the wall 250 or some combination thereof. The wall 250 can be constructed from any formable resilient material. In an exemplary embodiment, the wall 250 is constructed from a formable resilient polymer or plastic. FIGS. 28 and 30 show exemplary embodiments where further provided within the lumen 252 is a torqueable member 258 having a first end and a second end. The torqueable member 258 can either be located adjacent the wall 250 as shown in FIG. 28 or adjacent the centrally located conduit 254 as shown in FIG. 30. In both cases, the torqueable member 258 is mechanically connected to the handle 216 at the first end and to a point adjacent the deflection region 212 at the second end. The torqueable member 258 can be mechanically connected by methods known in the art, such as, for example adhesive bonding or by forming the handle around the torqueable member 258. Generally, the torqueable member 258 has a rigidity less than that of a steel pipe and more than that of a piece of string. The torqueable member 258 has a structure that resists rotational twisting when a rotational force is applied to an end. Further, the torqueable member 258 has a structure that will transmit the rotational force along its length. The torqueable member 258 facilitates the transmission of rotational forces from the handle 216 to the deflection region 212. The torqueable member 258 can be configured in many different ways; for example, it may include a helical coil, a braided sheath or other such devices. The torqueable member 258 can be constructed from a wide variety of materials, for example, coiled or braided metals or plastics or other such materials which exhibit the characteristics discussed herein.

Figure 31:
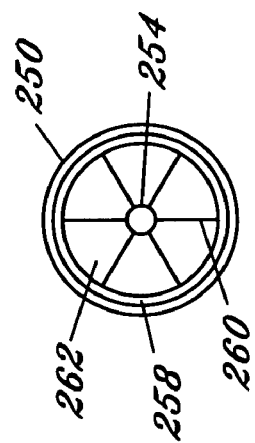
FIG. 31 is a sectional view of the body of FIG. 28 taken along line 31-31.
Figure 32:
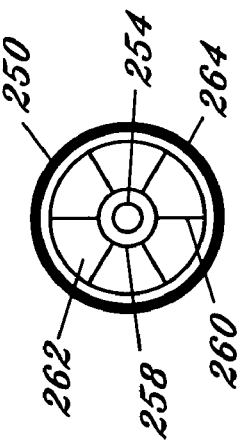
FIG. 32 is a sectional view of the body of FIG. 30 taken along line 32-32.

FIG. 31 is a sectional view taken along line 31-31 of FIG. 28. FIG. 31 shows a plurality of vanes 260 positioned between the torqueable member 258 and the conduit 254. The vanes 260 are provided to interconnect central components, such as the conduit 254 and the torqueable member 258 as shown in FIG. 31, with the outer components. The vanes 260 provide a support for and a connection between the central components and the outer components. Further, the vanes 260 define additional lumens 262 which can serve as passageway for fluids or additional components. Further, as shown in FIG. 32, which is a cross sectional view taken along line 32-32 of FIG. 30, the vanes 260 can also engage the torqueable member 258 when it is positioned adjacent the conduit 254. The vanes 260 can alternately extend the entire length of the body or some lesser portion thereof. It is contemplated that the vanes 260 can be created in a variety of ways, for example, by using a casting manufacturing process to create the device, formed during an extrusion process or by bonding to the wall 224 during an assembly process. Construction alternatives are discussed in further detail below.

Referring again to FIG. 32, the wall 250 can optionally contain a non-compressible element 264. The non-compressible element 264 can be a braided material disposed within the wall 250. The non-compressible element 264 is configured to maintain the shape of the body 210 under compressional loads, which can occur during use of the catheter system. The non-compressible element 264 can alternately extend the entire length of the catheter system or some lesser portion thereof. The non-compressible element 264 can be constructed in a variety of manners and from a variety of material. For example, the non-compressible element 264 can be a braided sleeve, a coiled tube or other such structures that afford the ability to resist a compression force. Further, the non-compressible element 264 can be constructed of metal, plastic or a combination thereof. In an exemplary embodiment the non-compressible element 264 is a braided metal sleeve that is cast within the wall 250.

Referring now to FIGS. 21 and 22, operation of the catheter system is now discussed. As shown in FIG. 21, the deflection region has a first non-actuated state. When tension is applied to an actuator member 222 disposed within catheter system, a force is transmitted to the distal region which causes the deflection structure to bend toward one side. The tension can be applied until a full actuation state occurs and the preferred deflection shape is reached as shown in FIG. 22. In the full actuation state the deflection region 212 takes a pre-determined shape that is defined by the specific physical construction of the longitudinal elements 224 and specific rigidity of the deflection wall. The structure of the longitudinal elements biases the deflection region to the non-actuated state. When the force is applied by the actuator member, the deflection shape and plane are defined by the specific alignment of the longitudinal elements and the variable rigidity of the material surrounding the longitudinal elements 224. For example, by defining the bend radii of different sections of the deflection region.

The catheter system of the invention can be constructed by techniques known in the art, such as using a single tube to manufacture the catheter. In the alternative, the catheter can be constructed by using a die or mandrel, over which the catheter is drawn or cast. One such method includes positioning all of the preformed components of the system around a central "lumen mandrel." Next, the material that makes up the walls of the catheter is cast around the preformed components. The preformed components can include the longitudinal elements, the actuator conduits, and any coils or other structural support components. The casting material is then allowed to harden and the "lumen mandrel" is removed. In this method, it is possible to vary the rigidity of different sections of the walls by casting materials which, upon hardening, have different rigidity. Further, the casting material may be "doped" to effect final rigidity of a selected portion of the walls. Alternatively, the components can be soldered together before casting to add strength and/or prevent movement of the components during construction.

Additional discrete deflection structure sections can be added to the catheter tip to form other desired deflection shapes.

A variety of modifications and variations of the present invention are possible in light of the above disclosure. It is therefore understood that, within the scope of the appended claims, the present invention may be practiced otherwise than as specifically described hereinabove.

What is claimed is:

1. A catheter system comprising:
   at least two longitudinal elements embedded within the circumference of a wall of a deflection region, the wall having a longitudinal axis and the longitudinal elements being substantially axially aligned with the longitudinal axis of the deflection region;
   at least two actuator members, the actuator members being configured to apply respective actuation forces to the deflection region, the deflection forces being substantially aligned with the longitudinal axis of the deflection region;
   wherein the longitudinal members and the actuation members are arranged radially around the wall of the deflection region relative to one another in a configuration to define a deflection plane and shape of the deflection region.

2. The catheter system of claim 1, wherein the longitudinal members and the actuation members are aligned at ninety degree increments around the wall of the deflection region.

3. The catheter system of claim 1, further comprising at least one rib along the wall.

4. The catheter system of claim 3, wherein at least one longitudinal member is provided within the at least one rib.

5. The catheter system of claim 1, wherein the body wall defines a lumen and a conduit is provided within the lumen.

6. The catheter system of claim 5, wherein the conduit is located in the center of the lumen.

7. The catheter system of claim 6, further comprising a torqueable member provided within the lumen.

8. The catheter system of claim 7, wherein the torqueable member is located adjacent the conduit.

9. The catheter system of claim 7, wherein the torqueable member is located adjacent the body wall.

10. The catheter system of claim 6, further comprising a plurality of vanes adjacent the torqueable member.

11. The catheter system of claim 1, further comprising a distal region.

12. The catheter system of claim 11, wherein the distal region includes a treatment tip.

13. The catheter system of claim 1, further comprising a non-compressible element.

14. The catheter system of claim 13, wherein the non-compressible element is provided adjacent the wall.

15. The catheter system of claim 13, wherein the non-compressible element is provided within the wall.

16. The catheter system of claim 13, wherein the non-compressible element is a braided sleeve.

17. The catheter system of claim 13, wherein the non-compressible element is a coil.

* * * * *

UNITED STATES PATENT AND TRADEMARK OFFICE
CERTIFICATE OF CORRECTION

PATENT NO.        : 7,955,298 B2
APPLICATION NO.   : 11/112100
DATED             : June 7, 2011
INVENTOR(S)       : Sean Carroll et al.

It is certified that error appears in the above-identified patent and that said Letters Patent is hereby corrected as shown below:

On the Title Page, (60), change "Jun. 13" to --Jun. 15--.
    In Column 12, at Line 41, change "deflection" to --actuation--.
    In Column 12, at Line 44, change "members" to --elements--.
    In Column 12, at Line 50, change "members" to --elements--.
    In Column 12, at Line 55, change "members" to --elements--.
    In Column 12, at Line 56, delete the word "body".
    In Column 12, at Line 65, delete the word "body".
    In Column 12, at Line 66, change "claim 6" to --claim 7--.

Signed and Sealed this
Tenth Day of July, 2012

David J. Kappos
*Director of the United States Patent and Trademark Office*